United States Patent
Liu

(10) Patent No.: US 11,448,375 B2
(45) Date of Patent: Sep. 20, 2022

(54) MULTIFUNCTIONAL ATMOSPHERE CANDLE

(71) Applicant: Shenzhen Zongli Technology Co. LTD, Shenzhen (CN)

(72) Inventor: WenFeng Liu, Shenzhen (CN)

(*) Notice: Subject to any disclaimer, the term of this patent is extended or adjusted under 35 U.S.C. 154(b) by 90 days.

(21) Appl. No.: 17/121,790

(22) Filed: Dec. 15, 2020

(65) Prior Publication Data

US 2021/0102673 A1 Apr. 8, 2021

(51) Int. Cl.
| | | |
|---|---|---|
| *F21S 10/04* | (2006.01) | |
| *F21S 6/00* | (2006.01) | |
| *A61L 9/03* | (2006.01) | |
| *A47F 3/00* | (2006.01) | |
| *A47F 11/10* | (2006.01) | |

(52) U.S. Cl.
CPC ............. *F21S 10/04* (2013.01); *A47F 3/001* (2013.01); *A61L 9/03* (2013.01); *F21S 6/001* (2013.01); *A47F 11/10* (2013.01)

(58) Field of Classification Search
CPC . F21S 10/04; F21S 6/001; A47F 3/001; A47F 11/10
See application file for complete search history.

(56) References Cited

U.S. PATENT DOCUMENTS

| | | | | |
|---|---|---|---|---|
| 6,468,071 | B2 * | 10/2002 | Zou | F21S 19/00 431/290 |
| 10,222,017 | B2 * | 3/2019 | Skiba | E05G 1/10 |
| 2005/0169812 | A1 * | 8/2005 | Helf | A61L 9/127 422/123 |
| 2015/0369432 | A1 * | 12/2015 | Li | F21V 23/003 362/249.02 |
| 2016/0109081 | A1 * | 4/2016 | Thompson | F21S 6/001 362/96 |

FOREIGN PATENT DOCUMENTS

| | | | | |
|---|---|---|---|---|
| CN | 107411448 A | * | 12/2017 | |
| WO | WO-03070065 A1 | * | 8/2003 | ............. A47F 11/10 |

* cited by examiner

*Primary Examiner* — Alexander K Garlen

(57) ABSTRACT

The present disclosure discloses a multifunctional atmosphere candle. The multifunctional atmosphere candle comprises cushion blocks, a shell, a rotating plate, a base plate, a candle-imitating lamp, an aromatherapy cabin and a gift lifting device, wherein the cushion blocks are symmetrically arranged below the base plate, the candle-imitating lamp is arranged on the top of the base plate, the shell is arranged on the top of the candle-imitating lamp, the rotating plate rotatably penetrates through the upper wall of the shell, the aromatherapy cabin is arranged in the shell, and the gift lifting device is arranged in the shell and arranged below the rotating plate. The present disclosure belongs to the technical field of lamps, and particularly relates to a multifunctional atmosphere candle which controls a gift to ascend and descend through the gift lifting device, gives surprise to others, releases aroma through the aromatherapy cabin and further emphasizes the atmosphere.

4 Claims, 2 Drawing Sheets

US 11,448,375 B2

MULTIFUNCTIONAL ATMOSPHERE CANDLE

TECHNICAL FIELD

The present disclosure belongs to the technical field of lamps, and particularly relates to a multifunctional atmosphere candle.

BACKGROUND

Atmosphere candles, belonging to atmosphere lamps, are mostly used for theme parks, hotels and homes and can provide illumination and emphasize atmosphere for couple dating, people can set favorite scene lighting effects according to individual lighting requirements (such as color, temperature, brightness and direction), and people can select and control changes of brightness, gray scale and color of light in different spaces and times according to respective requirements and scene conditions, but an atmosphere candle in the prior art only emphasizes atmosphere through illumination and is single in means and is poor in functionality.

SUMMARY

To solve the problem, the present disclosure provides a multifunctional atmosphere candle which controls a gift to ascend and descend through a gift lifting device, gives surprise to others, releases aroma through an aromatherapy cabin and further emphasizes the atmosphere.

To achieve the function, the technical scheme adopted in the present disclosure is as follows: a multifunctional atmosphere candle comprises cushion blocks, a shell, a rotating plate, a base plate, a candle-imitating lamp, an aromatherapy cabin and a gift lifting device, wherein the cushion blocks are symmetrically arranged below the base plate, the candle-imitating lamp is arranged on the top of the base plate, the shell is arranged on the top of the candle-imitating lamp, the rotating plate rotatably penetrates through the upper wall of the shell, the aromatherapy cabin is arranged in the shell, and the gift lifting device is arranged in the shell and arranged below the rotating plate; the gift lifting device comprises a driving motor, a first gear, a second gear, a lead screw, a lead screw pair, a fixed block, a connecting plate, a positioning rod, a movable sleeve block, a placing plate, a supporting rod, an auxiliary rod and an illuminating lamp, the driving motor is arranged on the top of the candle-imitating lamp and arranged at the lower end of the inner wall of the shell, the first gear is arranged at the output end of the driving motor, the fixed block is arranged below the upper wall in the shell, the lead screw is rotatably arranged in the fixed block, the second gear is arranged below the lead screw, the second gear is meshed with the first gear, the lead screw pair is connected to the lead screw in a sleeving mode, the connecting plate is arranged on the side face of the lead screw pair and located below the rotating plate, the placing plate is arranged on the top of the connecting plate, the supporting rod is arranged at the end, close to the lead screw pair, of the top of the placing plate, the auxiliary rod is arranged on the top of the supporting rod and obliquely arranged, the illuminating lamp is arranged below the end, away from the supporting rod, of the auxiliary rod, the gift can glitter on the placing plate through the illuminating lamp, and details and gloss of the gift can be comprehensively displayed through strong light irradiation, the positioning rod is arranged in the shell, the movable sleeve block is movably connected to the positioning rod in the sleeving mode, and the movable sleeve block is arranged on the side face of the connecting plate.

Further, the aromatherapy cabin comprises a cabin body, a heating rod, air holes and a liquid injection pipe, the cabin body is arranged in the shell, the heating rod is arranged in the cabin body, the air holes penetrate through the upper wall of the shell and are connected into the cabin body, and the liquid injection pipe penetrates through the upper wall of the shell and is connected into the cabin body.

Further, the air holes are obliquely arranged without influencing air flow, and can prevent dust from entering into the aromatherapy cabin to influence aromatherapy liquid.

Further, lamp belts are uniformly distributed on the outer side face of the shell so as to increase the lighting effect.

By adopting the structure, the present disclosure has the beneficial effects the multifunctional atmosphere candle provided by the present disclosure is easy to operate, compact in mechanism and reasonable in design, the gift lifting device is additionally arranged, the driving motor is used for controlling the placing plate to ascend and descend, the auxiliary rod is used for controlling a rotating rod to be turned on, the illuminating lamp illuminates the gift on the placing plate, details of gifts can be comprehensively displayed through strong lamplight irradiation, the value of the gift can be fully displayed, the mind of others is better reflected, and surprise can be given to others.

Wherein, 1, cushion block; 2, rotating plate; 3, base plate; 4, candle-imitating lamp; 5, aromatherapy cabin; 6, gift lifting device; 7, driving motor; 8, first gear; 9, second gear; 10, lead screw; 11, lead screw pair; 12, fixed block; 13, connecting plate; 14, positioning rod; 15, movable sleeve block; 16, placing plate; 17, supporting rod; 18, auxiliary rod; 19, illuminating lamp; 20, cabin body; 21, heating rod; 22, air hole; 23, liquid injection pipe; 24, lamp belt; and 25, shell.

DESCRIPTION OF THE EMBODIMENTS

The technical scheme in the present disclosure is clearly and completely described in the following with reference to the accompanying drawings. Apparently, the embodiments in the following description are merely a part rather than all of the embodiments of the present disclosure. Based on the embodiment in the present disclosure, all other embodiments obtained by the ordinary technical staff in the art under the premise of without contributing creative labor belong to the scope protected by the present disclosure.

In the description of the present disclosure, it needs to be illustrated that the indicative direction or position relations of the terms such as "center", "upper", "lower", "left", "right", "vertical", "horizontal", "inside" and "outside" are direction or position relations illustrated based on the accompanying diagrams, just for facilitating the description of the present disclosure and simplifying the description, but not for indicating or hinting that the indicated device or element must be in a specific direction and is constructed and operated in the specific direction, the terms cannot be understood as the restriction of the present disclosure. Moreover, the terms such as "first", "second" and "third" are just used for distinguishing the description, but cannot be understood to indicate or hint relative importance. The present disclosure is further described in conjunction with the following accompanying diagrams.

Figure 1:
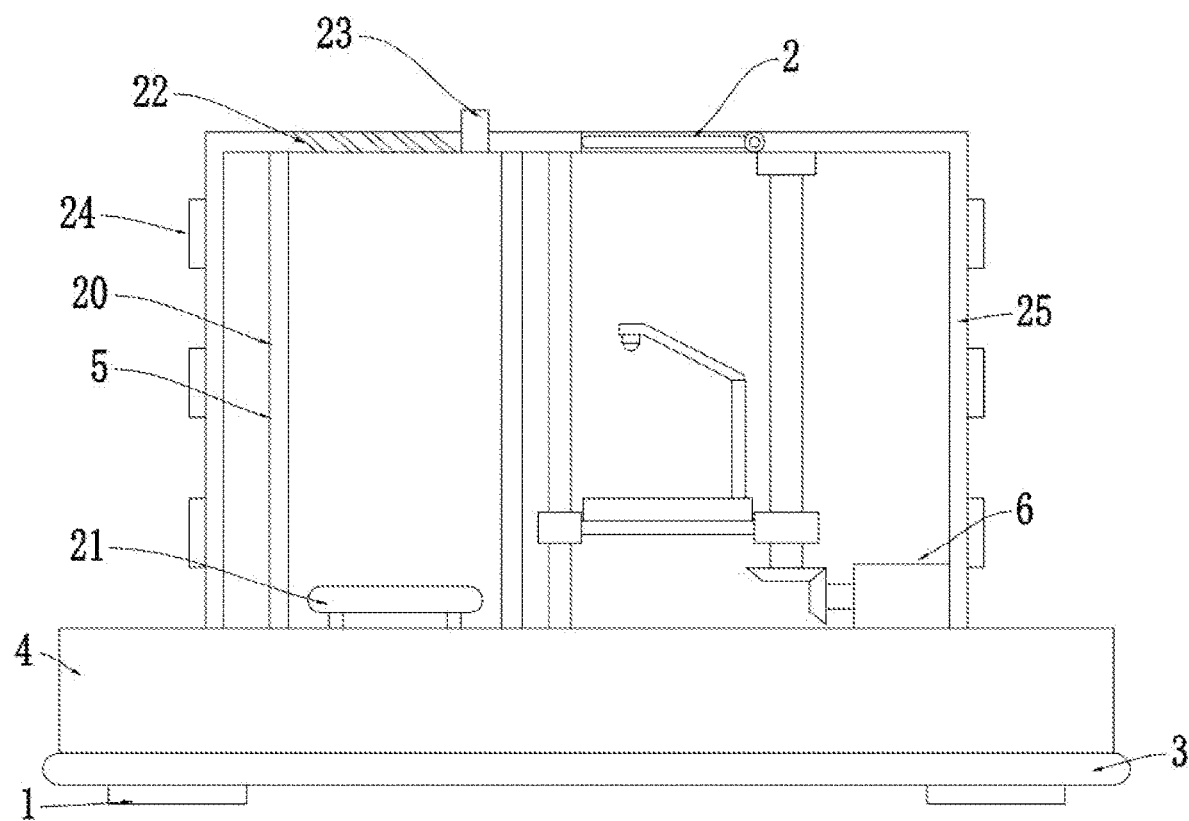
FIG. 1 is an overall structure diagram of a multifunctional atmosphere candle in the present disclosure.
Figure 2:
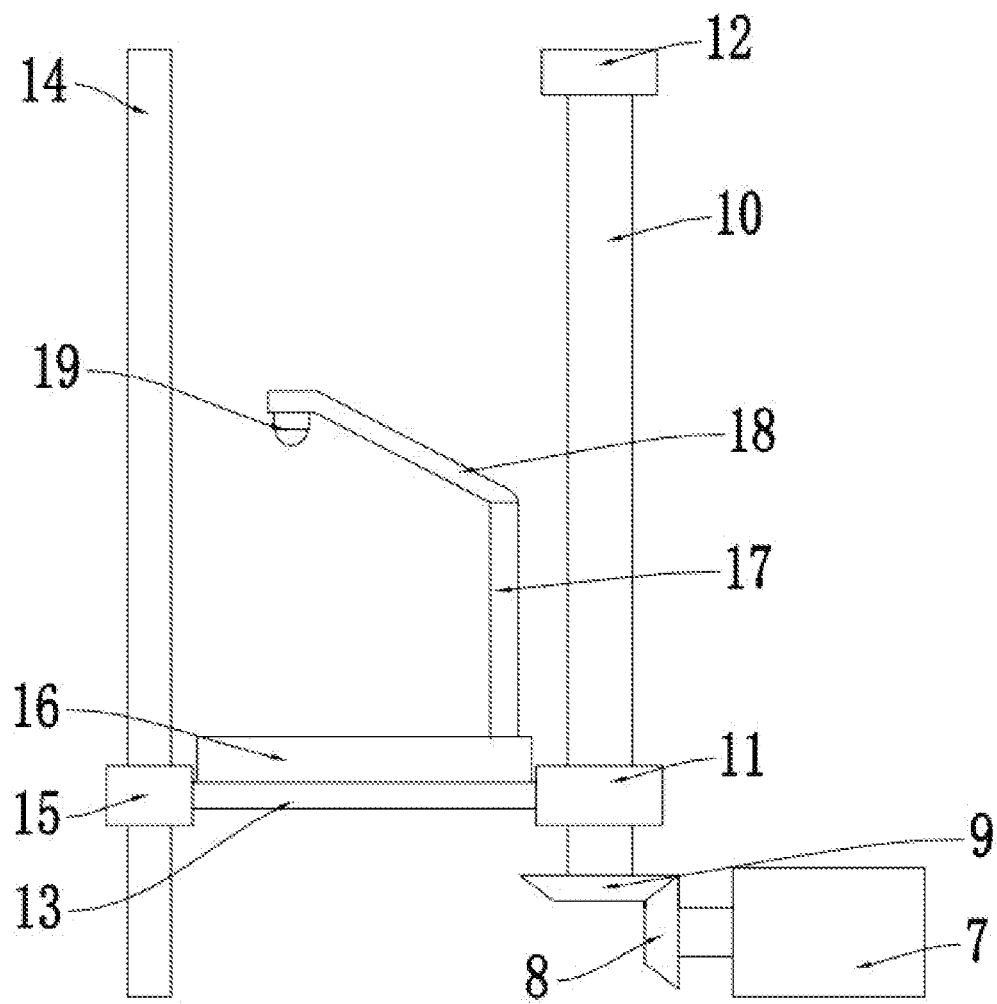
FIG. 2 is a structure diagram of a gift lifting device of a multifunctional atmosphere candle in the present disclosure.

As shown in FIG. 1 and FIG. 2, a multifunctional atmosphere candle in the present disclosure comprises cushion blocks 1, a shell 25, a rotating plate 2, a base plate 3, a candle-imitating lamp 4, an aromatherapy cabin 5 and a gift lifting device 6, wherein the cushion blocks 1 are symmetrically arranged below the base plate 3, the candle-imitating lamp 4 is arranged on the top of the base plate 3, the shell 25 is arranged on the top of the candle-imitating lamp 4, the rotating plate 2 rotatably penetrates through the upper wall of the shell 25, the aromatherapy cabin 5 is arranged in the shell 25, and the gift lifting device 6 is arranged in the shell 25 and arranged below the rotating plate 2; the gift lifting device 6 comprises a driving motor 7, a first gear 8, a second gear 9, a lead screw 10, a lead screw pair 11, a fixed block 12, a connecting plate 13, a positioning rod 14, a movable sleeve block 15, a placing plate 16, a supporting rod 17, an auxiliary rod 18 and an illuminating lamp 19, the driving motor 7 is arranged on the top of the candle-imitating lamp 4 and arranged at the lower end of the inner wall of the shell 25, the first gear 8 is arranged at the output end of the driving motor 7, the fixed block 12 is arranged below the upper wall in the shell 25, the lead screw 10 is rotatably arranged in the fixed block 12, the second gear 9 is arranged below the lead screw 10, the second gear 9 is meshed with the first gear 8, the lead screw pair 11 is connected to the lead screw 10 in a sleeving mode, the connecting plate 13 is arranged on the side face of the lead screw pair 11 and located below the rotating plate 2, the placing plate 16 is arranged on the top of the connecting plate 13, the supporting rod 17 is arranged at the end, close to the lead screw pair 11, of the top of the placing plate 16, the auxiliary rod 18 is arranged on the top of the supporting rod 17 and obliquely arranged, the illuminating lamp 19 is arranged below the end, away from the supporting rod 17, of the auxiliary rod 18, the positioning rod 14 is arranged in the shell 25, the movable sleeve block 15 is movably connected to the positioning rod 14 in the sleeving mode, and the movable sleeve block 15 is arranged on the side face of the connecting plate 13.

The aromatherapy cabin 5 comprises a cabin body 20, a heating rod 21, air holes 22 and a liquid injection pipe 23, the cabin body 20 is arranged in the shell 25, the heating rod 21 is arranged in the cabin body 20, the air holes 22 penetrate through the upper wall of the shell 25 and are connected into the cabin body 20, and the liquid injection pipe 23 penetrates through the upper wall of the shell 25 and is connected into the cabin body 20.

The air holes 22 are obliquely arranged.

Lamp belts 24 are uniformly distributed on the outer side face of the shell 25.

During specific use, firstly, the candle-imitating lamp 4 and the lamp belts 24 are turned on to emphasize the light atmosphere, then aromatherapy liquid is injected into the cabin body 20 through the liquid injection pipe 23, the heating rod 21 is started, the heating rod 21 is heated to promote evaporation of the aromatherapy liquid, the atmosphere is further emphasized, then the driving motor 7 is started to drive the lead screw 10 to rotate, and the lead screw 10 controls the lead screw pair 11 to move upwards; meanwhile, the connecting plate 13 and the placing plate 16 move upwards, the movable sleeve block 15 moves on the positioning rod 14, the auxiliary rod 18 makes contact with the rotating plate 2, the auxiliary rod 18 drives the rotating plate 2 to rotate, then the placing plate 16 is located on the upper wall of the shell 25, the prepared gift is placed on the placing plate 16, and then the driving motor 7 is started to control the gift to descend; and when required, the driving motor 7 is started to control the gift to ascend, and meanwhile, the illuminating lamp 19 is turned on to achieve a surprised effect.

The present disclosure and the embodiment thereof are described above, the description is not limited, only one of the embodiments of the present disclosure is shown in the accompanying drawings, and the actual structure is not limited in this way. In conclusion, if any person skilled in the art is inspired by the technical scheme, the structural mode and the embodiment similar to those of the technical scheme are not creatively designed under the condition of without departing from the creation purpose of the present disclosure, and the structural mode and the embodiment belong to the protection range of the present disclosure.

What is claimed is:

1. A multifunctional atmosphere candle comprising: cushion blocks, a shell, a rotating plate, a base plate, a candle-imitating lamp, an aromatherapy cabin and a gift lifting device, wherein the cushion blocks are symmetrically arranged below the base plate, the candle-imitating lamp is arranged on the top of the base plate, the shell is arranged on the top of the candle-imitating lamp, the rotating plate rotatably penetrates through the upper wall of the shell, the aromatherapy cabin is arranged in the shell, and the gift lifting device is arranged in the shell and arranged below the rotating plate; the gift lifting device comprises a driving motor, a first gear, a second gear, a lead screw, a lead screw pair, a fixed block, a connecting plate, a positioning rod, a movable sleeve block, a placing plate, a supporting rod, an auxiliary rod and an illuminating lamp, the driving motor is arranged on the top of the candle-imitating lamp and arranged at the lower end of the inner wall of the shell, the first gear is arranged at the output end of the driving motor, the fixed block is arranged below the upper wall in the shell, the lead screw is rotatably arranged in the fixed block, the second gear is arranged below the lead screw, the second gear is meshed with the first gear, the lead screw pair is connected to the lead screw in a sleeving mode, the connecting plate is arranged on the side face of the lead screw pair and located below the rotating plate, the placing plate is arranged on the top of the connecting plate, the supporting rod is arranged at the end, close to the lead screw pair, of the top of the placing plate, the auxiliary rod is arranged on the top of the supporting rod and obliquely arranged, the illuminating lamp is arranged below the end, away from the supporting rod, of the auxiliary rod, the positioning rod is arranged in the shell, the movable sleeve block is movably connected to the positioning rod in the sleeving mode, and the movable sleeve block is arranged on the side face of the connecting plate.

2. The multifunctional atmosphere candle according to claim 1, wherein the aromatherapy cabin comprises a cabin body, a heating rod, air holes and a liquid injection pipe, the cabin body is arranged in the shell, the heating rod is arranged in the cabin body, the air holes penetrate through the upper wall of the shell and are connected into the cabin body, and the liquid injection pipe penetrates through the upper wall of the shell and is connected into the cabin body.

3. The multifunctional atmosphere candle according to claim 1, wherein the air holes are obliquely arranged.

4. The multifunctional atmosphere candle according to claim 1, wherein lamp belts are uniformly distributed on the outer side face of the shell.

\* \* \* \* \*